US011197695B2

(12) United States Patent
Biedermann et al.

(10) Patent No.: US 11,197,695 B2
(45) Date of Patent: Dec. 14, 2021

(54) RECEIVING PART AND INSTRUMENT FOR HOLDING THE RECEIVING PART

(71) Applicant: BIEDERMANN TECHNOLOGIES GMBH & CO. KG, Donaueschingen (DE)

(72) Inventors: Timo Biedermann, Trossingen (DE); Dimosthenis Dandanopoulos, VS-Schwenningen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 24 days.

(21) Appl. No.: 16/055,691

(22) Filed: Aug. 6, 2018

(65) Prior Publication Data

US 2019/0046240 A1 Feb. 14, 2019

Related U.S. Application Data

(60) Provisional application No. 62/542,674, filed on Aug. 8, 2017.

(30) Foreign Application Priority Data

Aug. 8, 2017 (EP) .................................... 17185421

(51) Int. Cl.
*A61B 17/70* (2006.01)
*A61B 17/86* (2006.01)

(52) U.S. Cl.
CPC ...... *A61B 17/7032* (2013.01); *A61B 17/7076* (2013.01); *A61B 17/7086* (2013.01); *A61B 17/866* (2013.01)

(58) Field of Classification Search
CPC .......................................... A61B 17/70–7098
See application file for complete search history.

(56) References Cited

U.S. PATENT DOCUMENTS 6,540,748 B2    4/2003   Lombardo
8,025,683 B2    9/2011   Morrison
(Continued)

FOREIGN PATENT DOCUMENTS

CN         103431903 A        12/2013
DE    10 2013 100574 A1       7/2014
(Continued)

OTHER PUBLICATIONS

Extended European Search Report for Application No. 17185421.9, dated Feb. 9, 2018, 11 pages.

*Primary Examiner* — Nicholas J Plionis
(74) *Attorney, Agent, or Firm* — Lewis Roca Rothgerber Christie LLP (57) ABSTRACT

A receiving part of a bone anchoring device includes a channel adjacent a first end for receiving a bone fixation element, the channel forming two free legs each having an engagement structure for engaging a locking element to lock the bone fixation element in the channel, an outer surface portion, and at least one projection for engaging an instrument to connect the instrument to the receiving part. The projection projects radially outwardly from the outer surface portion, is spaced apart axially from the first end of the receiving part, and has a circumferential width less than a circumferential width of the legs. The projection has a first side wall that faces the first end. At least part of the first side wall is inclined towards the first end as the first side wall extends circumferentially, to form a region of the projection that narrows towards the first end.

17 Claims, 10 Drawing Sheets

(56) References Cited

U.S. PATENT DOCUMENTS

| | | | |
|---|---|---|---|
| 8,267,969 B2 | 9/2012 | Altarac et al. | |
| 8,414,588 B2* | 4/2013 | Stad | A61B 17/7085 606/246 |
| 8,998,958 B2 | 4/2015 | Dauster et al. | |
| 9,005,260 B2 | 4/2015 | Dauster et al. | |
| 2004/0111088 A1* | 6/2004 | Picetti | A61B 17/7032 606/265 |
| 2006/0025768 A1* | 2/2006 | Iott | A61B 17/7076 606/86 A |
| 2006/0111715 A1* | 5/2006 | Jackson | A61B 17/7028 128/897 |
| 2006/0116677 A1 | 6/2006 | Burd et al. | |
| 2006/0293692 A1* | 12/2006 | Whipple | A61B 17/7091 606/104 |
| 2007/0167954 A1* | 7/2007 | Sicvol | A61B 17/7037 606/104 |
| 2008/0140136 A1* | 6/2008 | Jackson | A61B 17/7037 606/328 |
| 2008/0154315 A1* | 6/2008 | Jackson | A61B 17/7035 606/309 |
| 2009/0143828 A1* | 6/2009 | Stad | A61B 17/7085 606/86 A |
| 2009/0198338 A1* | 8/2009 | Phan | A61B 17/7065 623/17.16 |
| 2010/0145394 A1 | 6/2010 | Harvey et al. | |
| 2010/0179602 A1* | 7/2010 | Dauster | A61B 17/7032 606/308 |
| 2011/0093021 A1* | 4/2011 | Fanger | A61B 17/7034 606/308 |
| 2012/0059426 A1* | 3/2012 | Jackson | A61B 17/68 606/300 |
| 2012/0179212 A1* | 7/2012 | Jackson | A61B 17/7032 606/328 |
| 2013/0018428 A1* | 1/2013 | Harper | A61B 17/7035 606/305 |
| 2013/0211465 A1* | 8/2013 | Savage | A61B 17/866 606/308 |
| 2013/0245705 A1* | 9/2013 | McBride | A61B 17/708 606/86 R |
| 2013/0261679 A1* | 10/2013 | McBride | A61B 17/708 606/86 A |
| 2014/0236236 A1 | 8/2014 | Krüger | |
| 2015/0039035 A1* | 2/2015 | Kruger | A61B 17/7082 606/264 |
| 2015/0313645 A1 | 11/2015 | Hansell | |
| 2015/0320468 A1* | 11/2015 | Kruger | A61B 17/7032 606/331 |
| 2017/0128104 A1* | 5/2017 | Nichols | A61B 17/8605 |

FOREIGN PATENT DOCUMENTS

| | | |
|---|---|---|
| EP | 3 120 791 A1 | 1/2017 |
| GN | 102202589 A | 9/2011 |
| WO | 2013/034351 A1 | 3/2013 |

* cited by examiner

RECEIVING PART AND INSTRUMENT FOR HOLDING THE RECEIVING PART

CROSS REFERENCE TO RELATED APPLICATION(S)

The present application claims priority to and the benefit of U.S. Provisional Patent Application No. 62/542,674, filed Aug. 8, 2017, the contents of which are hereby incorporated by reference in their entirety, and claims priority from European Patent Application EP 17 185 421.9, filed Aug. 8, 2017, the contents of which are hereby incorporated by reference in their entirety.

BACKGROUND

Field

The invention relates to a receiving part of a bone anchoring device, to an instrument for use with the receiving part in surgery, and to a system including the instrument and the receiving part. Such a receiving part is generally configured to connect a fixation element such as a rod with an anchoring element that can be inserted in a bone. The receiving part may be a separate member or it may be integrally formed with the anchoring element. The instrument is adapted to hold the receiving part in various applications before and/or during surgery, and may therefore be embodied, e.g., as an approximator, an extension device, a head placer, a reduction tool, etc.

Description of Related Art

A system for introducing an elongated spinal rod to a head of a monoaxial bone fastener device is known, for example, from US 2006/0025768 A1. The head includes a top surface, a bottom surface, and a U-shaped channel defining two legs. Each of the legs has two lateral end faces facing the channel. Recesses are formed in the end faces to define a seat for secure engagement with an instrument for handling the bone fastener or for introducing the spinal rod into the U-shaped channel. Also, an outer surface portion of each leg sidewall is provided with a curved shoulder which defines an arc-shaped cavity configured to receive a portion of another instrument for holding the head.

U.S. Pat. No. 8,267,969 B2 discloses a screw system for use in stabilization of bone structures. The screw system includes a screw, a retaining ring, a coupler, and a seat which receives the rod in a rod channel. On the outside surface of the seat, a flange is formed adjacent a top end of the seat. The flanges extend along the entire length of the legs in the circumferential direction. The flanges and/or the recesses allow gripping the seat using an instrument.

U.S. Pat. No. 6,540,748 B2 discloses a surgical screw system, wherein the U-shaped channel defines two lateral legs at a receiver member. Adjacent a top end of the receiver member, a flange extends at the legs along the entire length in the circumferential direction.

U.S. Pat. No. 8,025,683 B2 describes a surgical implant having a head with spaced-apart posts. A rod receiving area juxtaposes the posts. Each post has an outward side face having a vertically extending cylindrical surface adjacent a top end from which a generally inwardly directed undersurface extends in a circumferential direction. A cylindrical recess or bore penetrates the undersurface and is torsionally engageable with an inward facing tubular protrusion of a surgical tool.

U.S. Pat. No. 8,998,958 B2 describes a locking device introducer instrument for a rod fixation assembly. A receiver for receiving the rod is provided with an annularly extending flange at its legs which is penetrated by a release aperture that allows releasing of a locking ring retained in a groove formed at an inner bore of the receiver.

U.S. Pat. No. 9,005,260 B2 describes a receiver body for a spinal fixation system. Flanges extend circumferentially at each of the legs at a distance from the top end of the receiver body, wherein each flange is provided with two circular segments and a flat segment in which a radial bore is formed that provides for a pivot attachment point for external instruments. Further, one of the flanges is provided with an axial cutout or channel. A mechanism is thus provided for locking the radial position of the instrument after the instrument's attachment members are passed over the flat segments and rotated or "twisted" around beneath the circular segments. After the instrument is twisted over the circular segment, a pin or nail protuberance on the instrument can be inserted or engaged with the axial cutout or channel to lock the radial position of the instrument on the receiver body.

SUMMARY

It is an object of the present invention to improve the connection between a receiving part and an instrument for holding the receiving part, and/or to improve the ease of an attachment process of the instrument to the receiving part.

According to embodiments of the invention, a receiving part is provided which includes at least one projection, preferably two projections at opposed locations, at an outer surface portion thereof. The projection is configured to be engaged by a mating engagement recess formed at an instrument for holding the receiving part. A form-fit connection between the instrument and the receiving part is achieved by the engagement. Moreover, the projection includes a shape which tapers in a direction towards the top end of the receiving part. As a consequence, when an instrument is to be attached to the receiving part, wherein the projection of the receiving part is to be received by a corresponding recess of the instrument, the tapered shape of the projection allows for a self-alignment of the instrument with respect to the receiving part, and thus allows guiding of the instrument into the correct position and posture before establishing the form-fit connection. The tapered shape thus supports and improves the attachment process.

Moreover, the tapered shape allows for a unique spatial structure of the projection, which provides for a form-fit connection between the receiving part and the instrument, thereby securing the spatial orientation of the instrument with respect to the receiving part during a holding operation.

Still further, by providing a projection at the side of the receiving part which is received in a recess at the side of an instrument, a particular advantage arises in that less space is available for body tissue or fluids to accumulate in hidden corners at the receiving part. The projection is exposed to the outside, and the tissue and/or fluids may not easily adhere to the projection in considerable amounts as compared with, e.g., a recessed structure. Accordingly, the ease of surgical operations is improved.

The shapes of the projection of the receiving part and of the recess at the instrument need not be identical. Rather, the dimension of the projection (e.g., in plan-view) can be smaller than that of the recess of the instrument, as long as a form-fit connection is maintained and a mutual translation and rotation is ruled out. Nevertheless, a small amount of tolerance or play may be acceptable to allow for easily finding a correct orientation of the instrument with respect to the receiving part, or to allow tissue and/or fluids to escape during attachment.

In more specific embodiments, the projection may have a triangular shape, wherein for example two side walls extend towards the top end of the receiving part in an inclined manner, thereby approaching each other adjacent a top corner of the triangular shape. An opposite side wall faces the bottom end of the receiving part. A projection having such a shape provides for a simple structure, is easy to manufacture, establishes an efficient tapering structure, and guarantees a stable form-fit connection. The side walls of the triangular shape may also be planar, or may be concavely or convexly curved. Also, the corners of the triangle may be more or less rounded, or even cut off, to avoid sharp tips. The side walls, in particular the side wall facing the bottom end of the receiving part, may be undercut to improve the connection between the projection and the recess at the instrument.

According to further embodiments of the invention, an instrument is provided which is configured to hold the receiving part as described above. Such an instrument may for example be an approximator, a head placer, a rod reducing tool, a head extension device, or the like, and the invention is not limited to the specific application or use of the instrument. The instrument includes a tubular holding member and may or may not include further members, e.g., further tubular members or sleeves guided by the holding member to perform a specific application. Drive mechanisms and/or coupling members for driving the one or more tubular members may also be provided.

The tubular holding member holds the receiving part via an engagement recess which is configured and shaped to receive the projection of the receiving part as indicated above. The holding member may have a first arm and a second arm that are movable relative to each other, between an open position in which the receiving part is insertable between the first arm and the second arm, and a closed position in which the receiving part is held between the first arm and the second arm. The direction of movement between the arms may include an expansion or spreading of the arms. In one embodiment, the expansion may originate from a rotation of the arms about a pivot point arranged at a distance from the distal ends of the arms.

According to specific embodiments, a guiding channel forming side walls on the arms may be arranged at the distal end of one arm or both arms. The guiding channel extends from the distal end up to the engagement recess, and serves to align the instrument with the receiving part and to guide the projection therethrough and into the engagement recess.

The side walls of the guiding channel face each other and are arranged to abut on respective side walls of the projection of the receiving part which approach each other in a direction towards the top end of the receiving part. Due to the resulting inclination of the side walls of the projection with respect to an axis parallel to a central axis of the receiving part, which is also substantially the axis along which the instrument approaches and engages the receiving part, a respective side wall of the guiding channel experiences a rotational force while sliding down along the corresponding side wall of the projection. The instrument is thereby rotated and aligned during the sliding contact, such that the projection enters the guiding channel and eventually enters the engagement recess formed at a distance from the distal ends of the arms.

In a more specific embodiment, a base or bottom surface of the guiding channel extending between the side walls is inclined with respect to a central axis of the tubular holding member. This allows for a smooth expansion of the arms until the projection snaps into the engagement recess of the instrument to establish the form-fit connection.

BRIEF DESCRIPTION OF THE DRAWINGS

Further aspects and advantages will become apparent by a detailed explanation of embodiments when taken in conjunction with the appended drawings. In the drawings.

DETAILED DESCRIPTION

Figure 1:
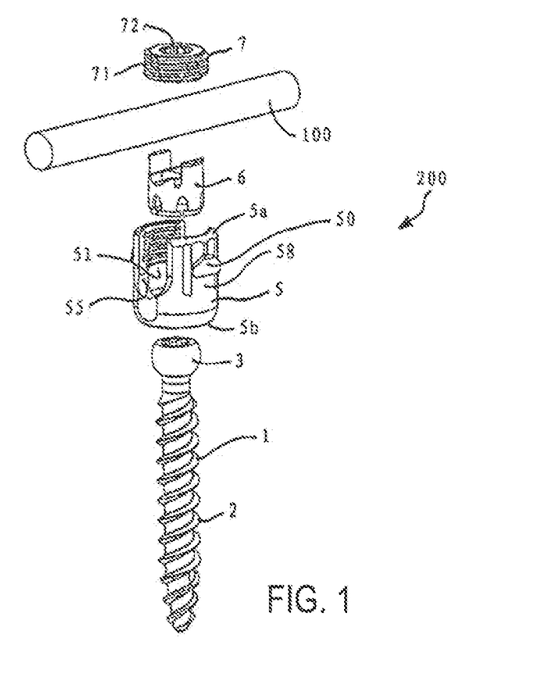
FIG. 1 shows a perspective view of a polyaxial bone anchoring device including a receiving part, according to a first embodiment of the invention.
Figure 2:
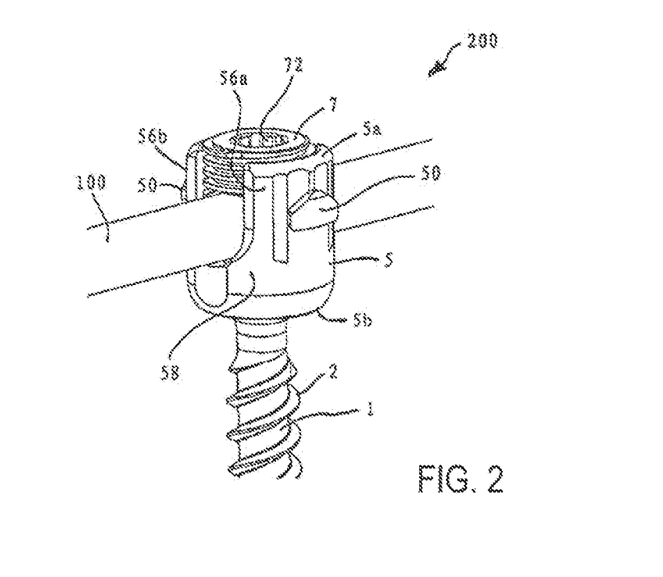
FIG. 2 shows an enlarged view of the bone anchoring device of FIG. 1 in an assembled state.
Figure 3:
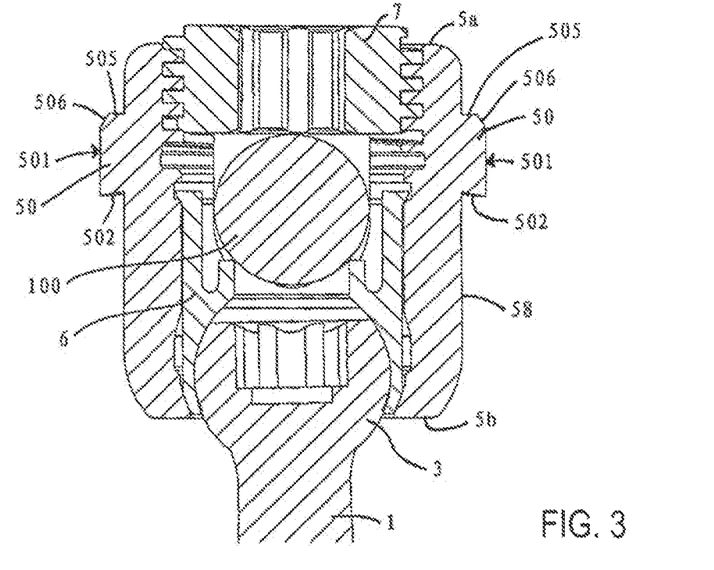
FIG. 3 shows a cross-sectional view of the bone anchoring device shown in FIG. 2.

With reference to FIGS. 1-6, a first embodiment of a receiving part 5 is described. FIGS. 1 and 2 provide an overview of a polyaxial bone anchoring device 200 which includes the receiving part 5. The bone anchoring device 200 further includes an anchoring element 1 having a head 3, a shank 2 provided with a bone thread for anchoring in a bone, a pressure element 6 adapted to exert pressure onto the head 3 when assembled in the receiving part 5, and a locking element 7 that has an external thread 71 for cooperating with an internal thread 54 of the receiving part 5 in order to exert pressure onto a spinal fixation element 100 received in the receiving part 5 and/or the pressure element 6. In this embodiment, the external thread 71 is a flat thread and the locking element 7 is further provided with an engagement feature 72, which may be hex-shaped, torx-shaped, or otherwise shaped as known in the art. The locking element 7 is herein provided as a single piece setscrew, but modified embodiments may also include other kinds of locking elements such as dual inner screws, etc.

The pressure element 6 has a seat for receiving the spinal fixation element 100 and two upwardly extending flexible legs, with each leg having a laterally protruding flange at its free end which allows for latching-in into corresponding recesses provided in the inner bore 51 of the receiving part 5 to prevent a further upward movement of the pressure element in the receiving part, when the head 3 of anchoring element 1 is inserted through a bottom opening 53 of the receiving part into an accommodation space 52 of the receiving part 5.

The pressure element 6 is further provided with a spherically-shaped recess at its bottom side configured to receive the spherical head 3 of the anchoring element 1. Flexible flanges extend at the distal end of the pressure element, which may extend around a maximum diameter portion of the spherical head 3 in order to frictionally clamp the head when it is introduced into the accommodation space 52 of the receiving part 5 and pressed against the pressure element 6, which in turn is prevented from an upward movement by the engagement between the legs of the pressure element and the latching recess of the receiving part. The accommodation space 52 has an increased width as compared with the substantially cylindrical bore 51 of the receiving part 5, in order to allow expansion of the flanges during insertion of the head 3.

It is noted that modified embodiments of the invention may include other types of pressure elements, and the invention is not limited to the specific kind of pressure element. In specific embodiments, a pressure element may even be omitted.

With reference to FIGS. 4A-6, the receiving part 5 is described in more detail. The receiving part 5 has a top or first end 5a and a bottom or second end 5b, and a substantially cylindrical bore 51 extends from the first end 5a in a direction towards the second end 5b. The inner bore 51 is coaxial with a central axis C of the receiving part 5 that extends through the first and second ends 5a, 5b. A channel 55 for receiving the spinal fixation element, which may be U-shaped or V-shaped, extends from the first end 5a in a direction towards the second end 5b. An axis D of the channel 55 extends perpendicular to the central axis C. The channel 55 defines two free legs 56a, 56b at the receiving part 5.

Figure 5A:
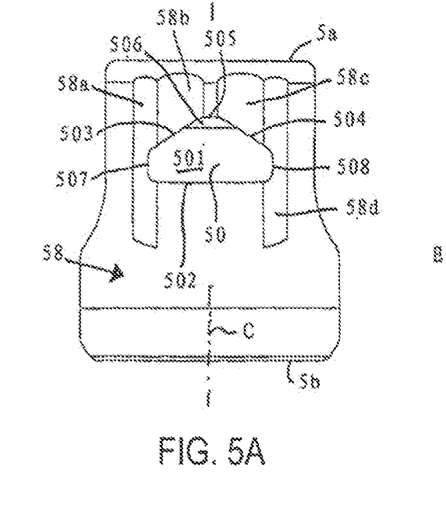
FIG. 5A shows a side view of the receiving part according to the first embodiment.

The receiving part 5 has an outer surface portion 58 which has a generally cylindrical contour. The term "generally" encompasses minor deviations, such as a recessed flat portion beneath the U-shaped channel 55 on each side of the receiving part 5 and longitudinal grooves extending from the first end 5a at each of the legs 56a, 56b in a direction parallel to the central axis C, as shown in FIG. 5A, which are due to the shaping process of various sidewalls of projection 50, to be described in greater detail below.

Figure 4A:
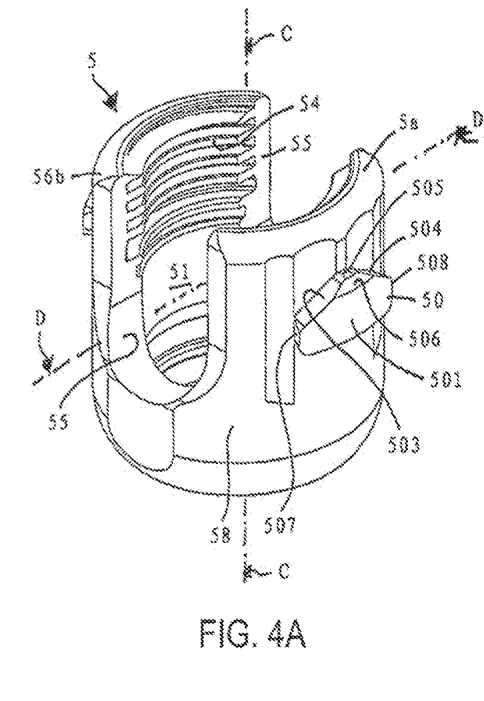
FIG. 4A shows a perspective view of the receiving part of the first embodiment, from a top perspective.
Figure 4B:
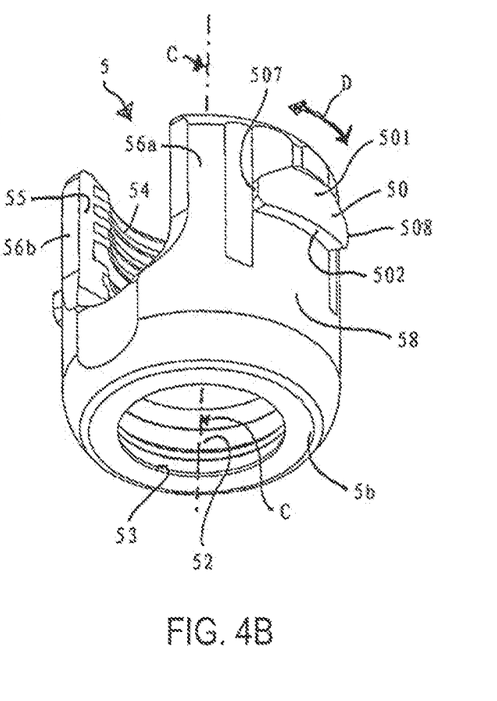
FIG. 4B shows a perspective view of the receiving part of the first embodiment, from a bottom perspective.

As can best be seen in FIGS. 4A and 4B, the projection 50 is formed on the outer surface portion 58 on each of the legs 56a, 56b of the receiving part 5. In the plan-view onto the projection 50 in FIG. 5A, the projection 50 is provided with a substantially triangular shape and is arranged symmetrical with respect to an axis parallel to the central axis C. One corner 505 of the projection extends in a direction toward the top or first end 5a and an opposite edge or sidewall 502 faces the bottom or second end 5b. The projection 50 is formed with a top surface 501 extending parallel to the cylindrical contour of the outer surface portion 58. The height of the projection 50 with respect to the outer surface portion 58 is less than a width of the projection 50 between a left-side corner 507 and a right-side corner 508 as measured in a circumferential direction, and is less than a length of the projection 50 measured between the top corner 505 and the opposite sidewall 502 facing the bottom or second end 5b in a direction parallel to the central axis C.

Further, a width between corners 507, 508 in a circumferential direction is larger than a length of projection 50 between the top corner 505 and the opposite sidewall 502 in a direction parallel to the central axis C. The sharp tips at the left-side and right-side corners 507, 508 are removed to create flattened corner profiles. As will be described below with respect to the function of the projection 50, the sidewall 502 facing the second end 5b is provided with an undercut, as can best be seen in FIG. 6. In other words, a surface of the sidewall 502 is inclined with respect to a plane perpendicular to the central axis C. This undercut allows for an improved form-fit connection between an instrument 60 (see below) and the receiving part 5.

At the top corner 505 facing the first end 5a of the receiving part 5, a chamfer 506 is formed to yield a surface at the top corner 505 which is inclined with respect to the central axis C. This chamfer increases a sliding contact area with respect to an instrument that is attached to the receiving part 5. As a consequence, arms of the instrument are smoothly spread and expanded by such contact.

Figure 5B:
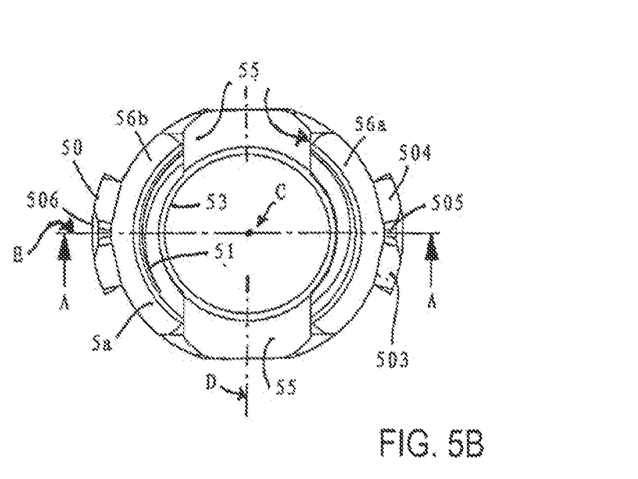
FIG. 5B shows a top view of the receiving part according to the first embodiment.
Figure 6:
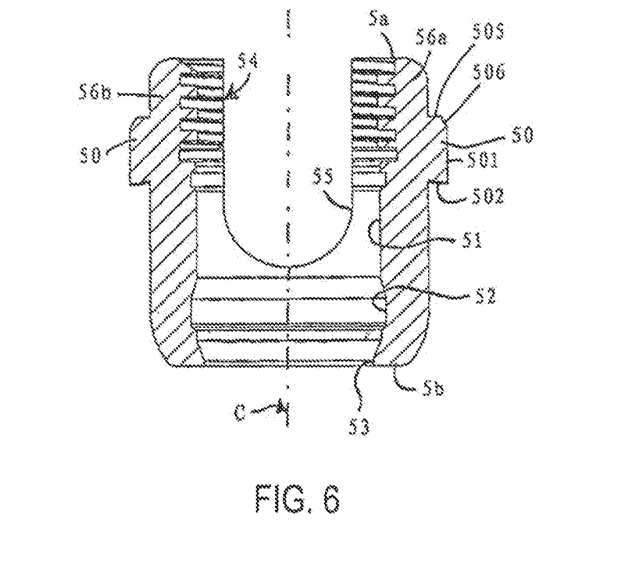
FIG. 6 shows a cross-sectional view of the receiving part of the first embodiment, the cross-section taken along line A-A in FIG. 5B.

As can particularly be seen in FIGS. 4A and 4B, the projections 50 are arranged at about a center of each leg, at a distance from the first end 5a and the second end 5b in a direction parallel to the central axis C, and with respect to each of the lateral end faces of the legs 56a, 56b in a circumferential direction. In other words, the dimensions of the projections 50 are smaller than those of the legs 56a, 56b in both a direction parallel to the central axis C and a circumferential direction. Further, the projections 50 are located opposite each other with respect to the central axis C, and are arranged along an axis E, which is perpendicular to the central axis C and the axis D of the channel 55, respectively, as can be seen in FIG. 5B. It is noted that in modified embodiments, the projections 50 may be arranged offset from a center position at the legs, or may be positioned differently axially, for example, closer to the bottom end of the receiving part 5 beneath the legs.

With reference to FIGS. 4A, 5A, and 5B, the triangular structure of the projection 50 leads to a taper that narrows towards the top or first end 5a. Between the left-side corner 507 and the top corner 505 and between the right-side corner 508 and the top corner 505, edges or sidewalls 503, 504 extend substantially radially from the outer surface portion 58 of the receiving part 5. In this embodiment, the sidewalls 503 and 504 are substantially planar and terminate at the rounded structures of the corners 505, 507, and 508. Each of the sidewalls 503, 504 is inclined with respect to a direction parallel to the central axis C. As will be explained below, the sidewalls 503, 504 allow for a self-alignment of an instrument that is guided towards and onto the receiving part 5. The corner 505 spans an angle α of more than 90 degrees (see FIG. 15A). However, in other embodiments, the angle at the top corner 505 may also be equal to 90 degrees or smaller than 90 degrees.

With reference to FIGS. 7-12D, an instrument 60 for use with a receiving part such as that of the first embodiment is shown, with respect to details of its distal end section. The instrument 60 includes a tubular holding member 10, which is configured to be attached to the receiving part 5 and to hold the same in a form-fit connection. The holding member 10 has two arms 12a, 12b, which are separated by a slot 18 which extends from a distal end 10a, 10b of the respective arms. At a distance from the distal end 10a, 10b, a connecting portion 13 is provided at both sides of the slot 18 (only one side is shown) that connects the arms 12a, 12b together. The connecting portion 13 has the shape of an arcuate bridge with a curvature that is concave when viewed from the distal end 10a, 10b. The thickness of the connecting portion 13 and the curvature is selected such that the connecting portion 13 acts as a spring between the arms 12a, 12b. The connecting portion 13 may form a fulcrum that permits the arms 12a, 12b of the holding member 10 to perform a pivoting movement like pliers, such that a movement of the arms 12a, 12b towards each other at a proximal end (not shown) results in spreading the arms 12a, 12b at the distal end 10a, 10b. Thereby, an open position of the holding member 10 is defined in which a receiving part can be inserted between the arms 12a, 12b adjacent the distal end 10a, 10b. When the arms 12a, 12b are released at the proximal end (not shown), the return force of the spring portion moves the arms 12a, 12b towards each other at the distal end 10a, 10b, whereby a closed position is defined in which the arms 12a, 12b are substantially parallel to each other.

The tubular holding member 10 has an engagement section 17 extending at the distal end 10a, 10b, and having a generally cylindrical outer contour with a reduced diameter as compared with a main section of the tubular holding member 10 to which it is connected via a conical transition section. The engagement section 17 of the tubular holding member 10 is configured to receive the receiving part 5 and provides the means for holding the same.

Figure 8A:
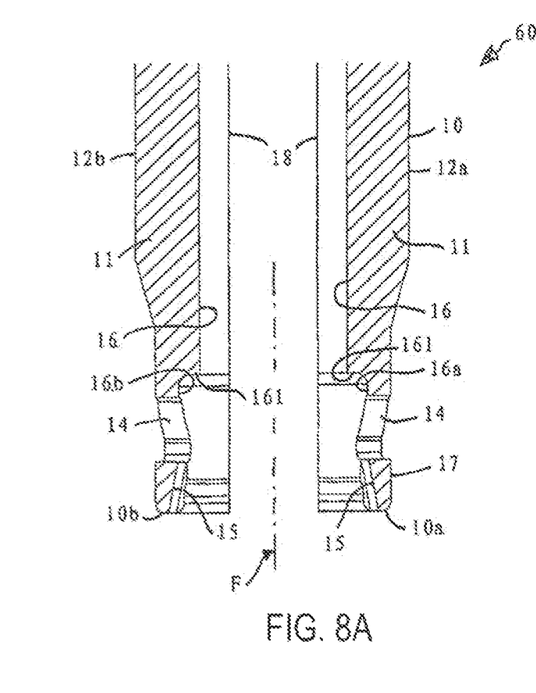
FIG. 8A shows a cross-sectional view of the instrument shown in FIG. 7.

As can particularly be seen in FIG. 8A, the tubular holding member 10 includes substantially cylindrical inner wall portions 16 at both arms 12a, 12b, wherein a section 16a, 16b of the inner wall portions 16 within the engagement section 17 are provided with an increased inner diameter such as to provide a complementary or mating shape for an upper portion of the receiving part 5. Also, annular shoulders 161 provided at the proximal end of sections 16a, 16b define an abutment face for the top or first end 5a of the receiving part 5 when it is inserted into the engagement section 17 of the instrument 60.

Figure 7:
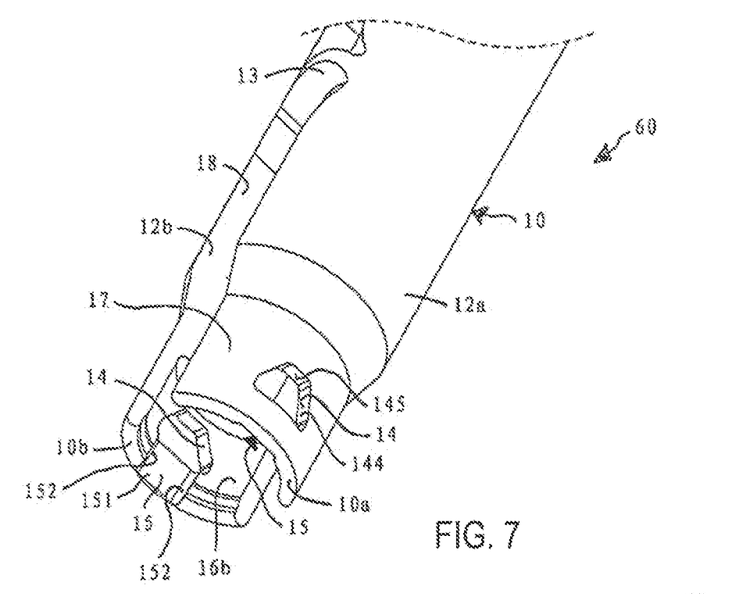
FIG. 7 shows a perspective view of an embodiment of an instrument.
Figure 8B:
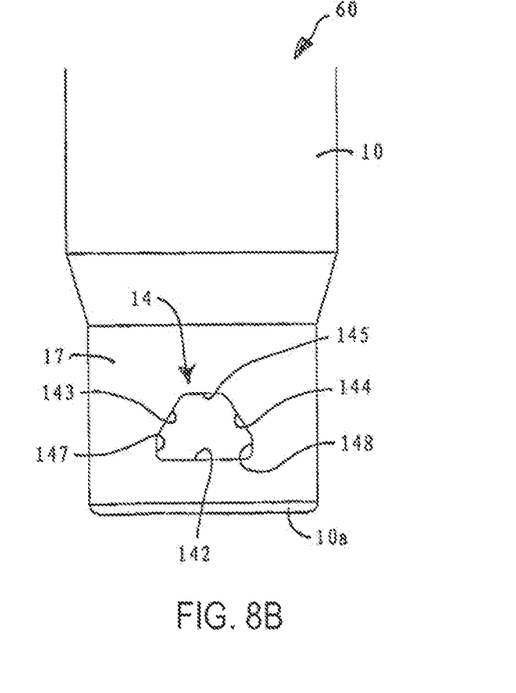
FIG. 8B shows a lateral side view of the instrument shown in FIG. 7.

With reference to FIGS. 7 and 8B, an engagement recess 14 is formed as a cutout in sections 16a, 16b of the inner wall portion 16 at each of the arms 12a, 12b. The engagement recess 14 has a generally triangular shape with corners 145, 147, 148 and sidewalls 142, 143, 144. As can be seen, tips of the triangular shape are cut off in order to avoid acute angles at the corners. The position of the engagement recess 14 within the engagement section 17, and particularly with respect to the enlarged diameter section 16a of the inner wall portion 16 and the annular shoulder 161, is such that when the receiving part 5 is introduced into the inner accommodation space of the engagement section 17, the projection 50 of the receiving part 5 may be received in the engagement recess 14 of the instrument 60.

Figure 9:
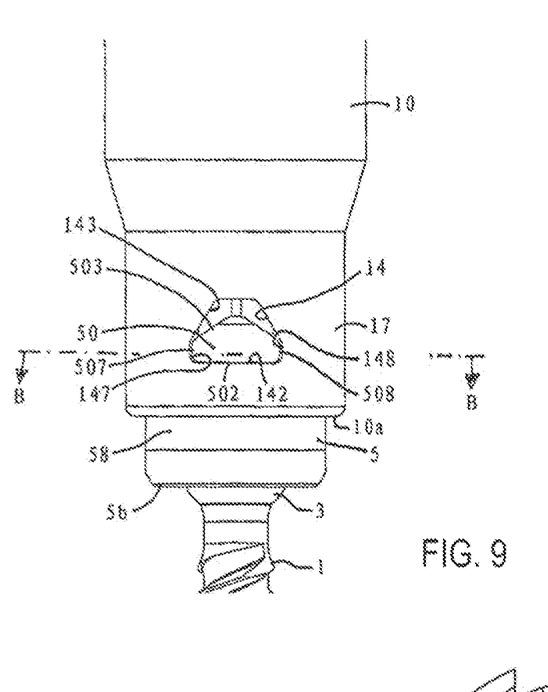
FIG. 9 shows the instrument of FIG. 7 attached to the receiving part of the first embodiment in a lateral side view.
Figure 10:
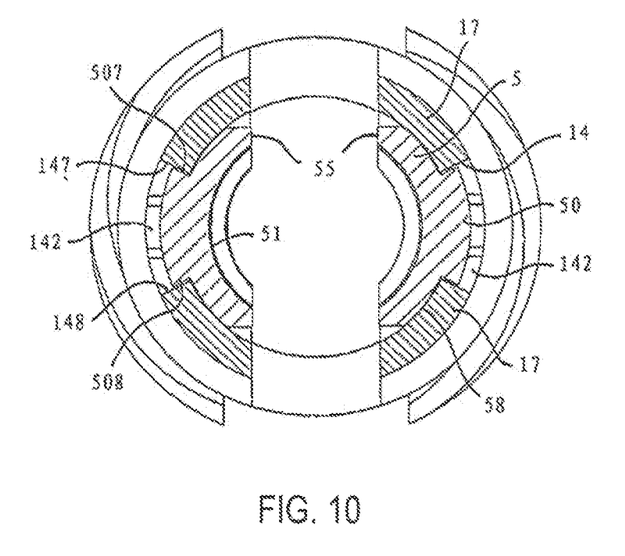
FIG. 10 shows a cross-sectional view of the receiving part and instrument shown in FIG. 9, the cross-section taken along line B-B in FIG. 9.

With reference to FIGS. 9 and 10, a state is shown wherein a receiving part 5 (assembled as part of a bone anchoring device) is received in the inner accommodation space of the engagement section 17 of the tubular holding member 10. As can be seen, the projection 50 is received in the engagement recess 14 of the holding member 10. Similar to the projection 50 of the receiving part 5, the engagement recess 14 of the instrument 60 has a tapered shape (in this embodiment: a triangular shape), wherein the taper is oriented away from the distal end 10a, 10b. The shapes of the engagement recess 14 and the projection 50 need not be identical, as can be seen in FIG. 9. Rather, it is sufficient to yield a form-fit connection between the instrument 60, or holding member 10, and the receiving part 5 by the mating shapes of the left- and right-side corners 507, 508 and the sidewall 502 of projection 50 with left- and right-side corners 147, 148 and sidewall 142 of engagement recess 14, respectively. Except for some tolerance or play, for example, as indicated in FIG. 9, the mating shapes of projection 50 and engagement recess 14 (almost) impede further translational movement in a direction along the central axis C, as well as rotation about axes C and E.

With reference to FIG. 10, the engagement recess 14 is formed as a cutout in the inner wall portion 16 of the tubular holding member 10. In other words, the engagement recess 14 is formed by an aperture, or opening extending through the inner wall portion towards an outer surface portion of the engagement section 17. This structure allows amounts of tissue or fluids assembling or accumulating around the projections 50 to easily escape through the engagement recess 14 when received therein. Nevertheless, modified embodiments in which the engagement recess 14 is formed as a groove within the inner wall portion 16, without extending to the outer surface portion, are also encompassed by the invention.

With reference to FIGS. 7 and 8A, a guiding channel 15 extends from the distal end 10a, 10b of each arm 12a, 12b and opens into the respective engagement recess 14. The guiding channel 15 is formed within section 16a, 16b of the inner wall portion 16 of the tubular member 10. The guiding channel 15 includes a substantially flat bottom surface 151 and two opposing sidewalls 152, and a width of the guiding channel 15 in a circumferential direction about a central axis F of the holding member 10 substantially corresponds to that of the engagement recess 14. It is possible, but not necessary, that a distance between the sidewalls 152 of the guiding channel 15 increases towards the distal end 10a, 10b. As can be seen in FIG. 8A, the bottom surface 151 of the guiding channel 15 is inclined with respect to the central axis F of the holding member 10. More specifically, the guiding channel 15, or its bottom surface, is inclined away from the central axis F as the guiding channel extends towards the distal end 10a, 10b, such that the mutual distance between, e.g., two opposed guiding channels 15 formed with respect to corresponding engagement recesses 14 at each of the arms 12a, 12b increases towards the distal end 10a, 10b even in the closed position. As will be explained below, the guiding channel 15 facilitates an alignment of the instrument 60 with the position of the projection 50 of the receiving part 5 during attachment of the instrument 60 to the receiving part 5.

Figure 11A:
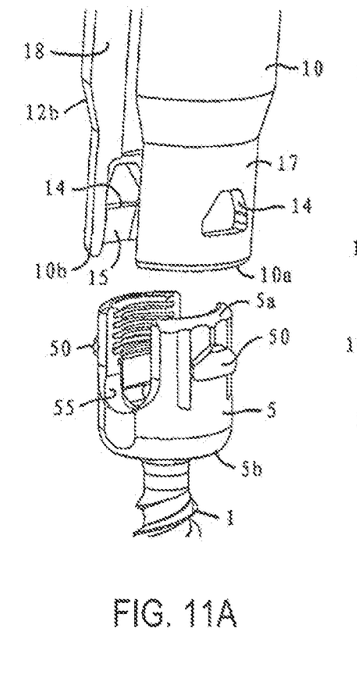
FIG. 11A shows, in a perspective view, a first state of attaching the instrument to the receiving part according to the first embodiment.
Figure 11B:
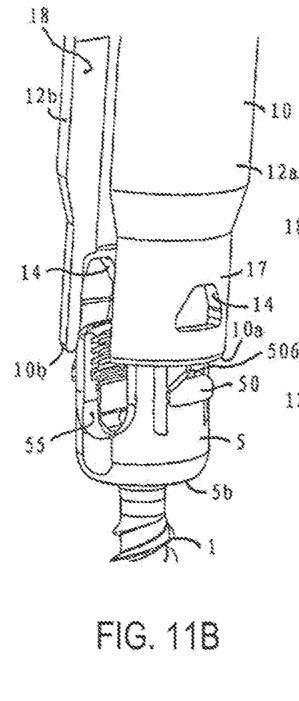
FIG. 11B shows, in a perspective view, a second state of attaching the instrument to the receiving part according to the first embodiment.
Figure 11C:
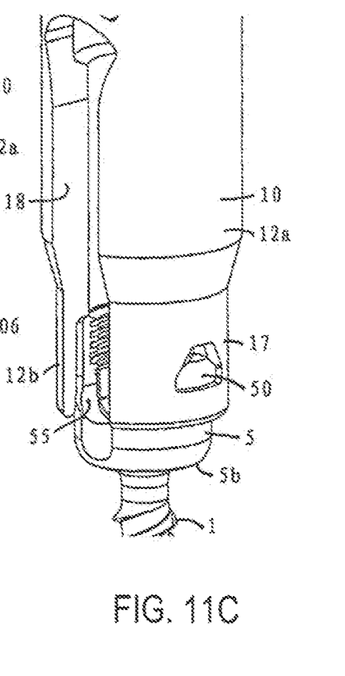
FIG. 11C shows, in a perspective view, a third state of attaching the instrument to the receiving part according to the first embodiment.
Figure 12A:
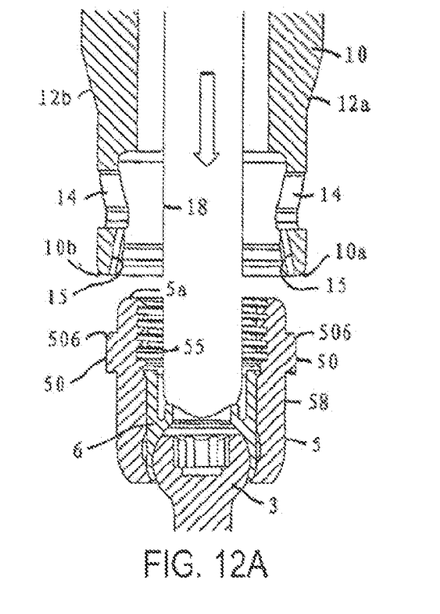
FIG. 12A shows, in a cross-sectional view, the first state of attaching the instrument to the receiving part according to the first embodiment.

With reference to FIGS. 11A-11C and 12A-12D, operation of the instrument 60 and the receiving part 5 during use is explained. FIGS. 11A and 12A show a first state of attaching the instrument 60 to the receiving part 5. The central axes C, F of the receiving part 5 and the tubular holding member 10 are manually aligned by the surgeon, and the instrument is guided to the receiving part 5.

Figure 12B:
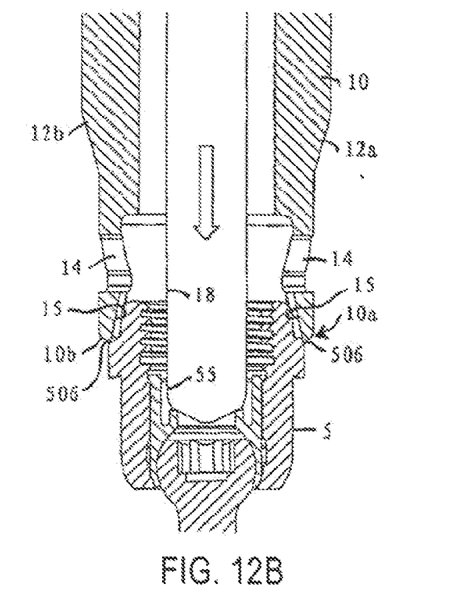
FIG. 12B shows, in a cross-sectional view, the second state of attaching the instrument to the receiving part according to the first embodiment.
Figure 12C:
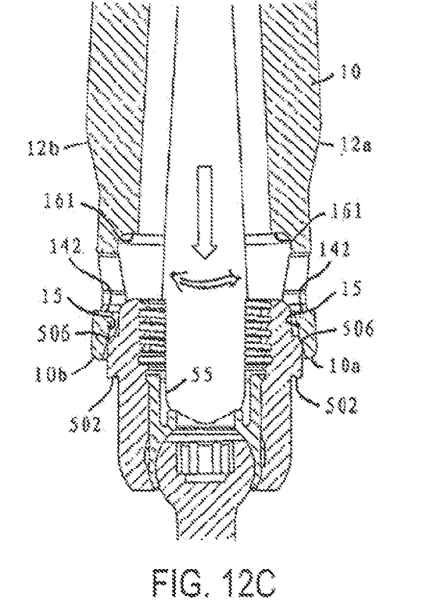
FIG. 12C shows, in a cross-sectional view, a further state between the second state and the third state of attaching the instrument to the receiving part according to the first embodiment.

In a second state shown in FIGS. 11B and 12B, the first end 5a of the receiving part 5 is guided into the accommodation space of the engagement section 17 until a point wherein the chamfer 506 at the top corner 505 of projection 50 comes into contact with the bottom surface of the guiding channel 15. Starting from this point, as can be seen in FIG. 12C, the chamfer 506 starts to slide on the bottom surface of guiding channel 15, wherein upon further introduction of the receiving part into the inner accommodation space of the engagement section 17, the arms 12a, 12b of the tubular holding member 10 start to spread and expand, yielding an open position of the instrument. During further insertion, the inclined sidewalls 503 or 504 may eventually abut on one of the sidewalls of the guiding channel 15 due to some misalignment of the instrument 60 with respect to the receiving part 5 in the circumferential direction. Due to the inclination of the sidewalls 503, 504, however, a rotational force is generated between the instrument and the receiving part 5, which aligns the instrument with respect to the receiving part 5. The projection 50 is then smoothly guided into the guiding channel 15 of the tubular holding member 10 of the instrument 60.

Figure 12D:
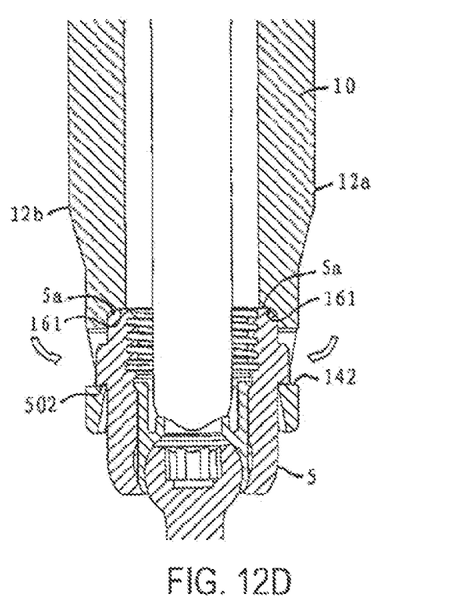
FIG. 12D shows, in a cross-sectional view, the third state of attaching the instrument to the receiving part according to the first embodiment.

With reference to FIGS. 11C and 12D, in a third state of operation, when an edge of the sidewall 502 of projection 50, which faces the second end 5b of the receiving part 5, passes over the end of the guiding channel 15, the projection 50 snaps into the engagement recess 14 of the tubular holding member 10 to establish a form-fit connection between the receiving part 5 and the instrument 60. Thereby, the undercut shape of the sidewall 502 further improves the connection, particularly when the corresponding mating sidewall 142 of the engagement recess 14 is also provided with a surface that is inclined in an outward direction. Moreover, in addition to the form-fit connection between the projection 50 and the engagement recess 14, at the same time when the projection 50 snaps into the engagement recess 14, the top or first end 5a of the receiving part 5 abuts on the annular shoulder 161 provided at the inner wall portion 16 of the tubular holding member 10. As a consequence, the receiving part 5 is firmly clamped in the inner accommodation space of the engagement section 17 of the instrument 60.

Figure 13:
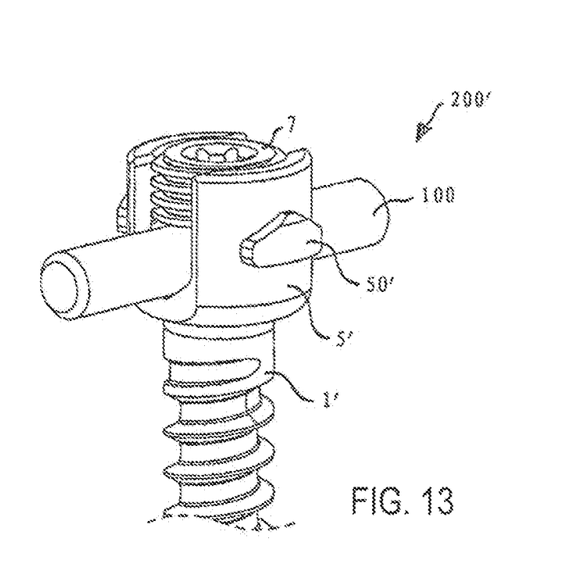
FIG. 13 shows a perspective view of a second embodiment of a receiving part which is formed integrally with an anchoring element in a monoaxial bone anchoring device.
Figure 14:
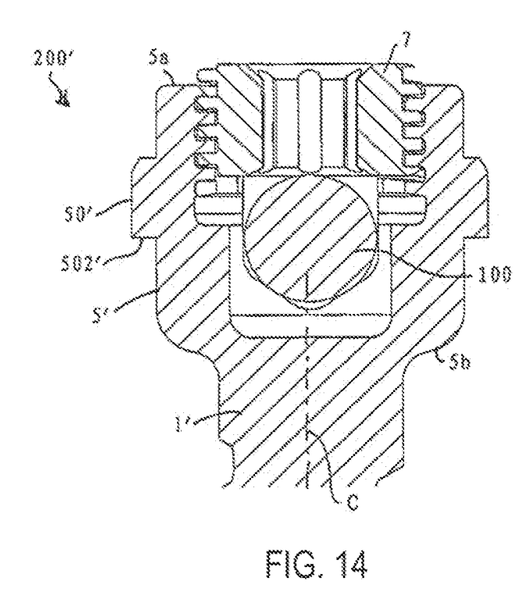
FIG. 14 shows a cross-sectional view of the bone anchoring device of FIG. 13.

With reference to FIGS. 13 and 14, a second embodiment of the present invention is shown. A monoaxial bone anchoring device 200' includes a receiving part 5' integrally formed with an anchoring element 1', and a locking element 7. Similar to the first embodiment, an outer surface portion of the receiving part 5' has a generally cylindrical contour and a projection 50' is formed at each of the legs, where the legs are formed by a channel for receiving a spinal rod 100. The shape, orientation and position of the projection 50' is almost identical to that of the first embodiment, i.e., the projection 50' is tapered and narrows in a direction towards the top or first end 5a. An instrument (not shown) for use with this receiving part 5' may be the same as that described above with reference to FIGS. 7-12D. Nevertheless, in this specific embodiment, the sidewall 502' of the projection 50' facing the bottom or second end 5b extends radially away from the central axis C of the receiving part 5', and is not provided with an undercut.

Figure 15A:
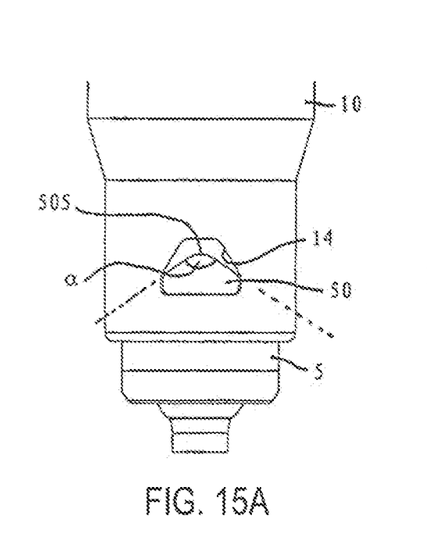
FIG. 15A shows the instrument attached to the receiving part according to the first embodiment in a side view.
Figure 15B:
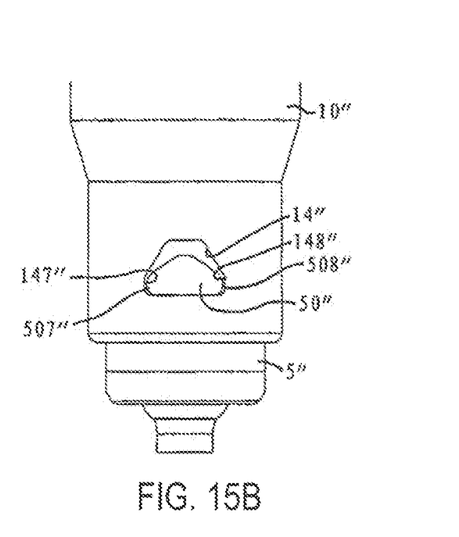
FIG. 15B shows a modified embodiment of an instrument attached to a receiving part in a side view.

With reference to FIGS. 15A-15E, modified embodiments of receiving parts and instruments are shown, respectively. The modifications mainly refer to the shapes of the projections and engagement recesses, respectively. In FIG. 15A, the projection 50 and engagement recess 14 of the first embodiment are repeated for reference only. In FIG. 15B, the left-side and right-side corners 507", 508" of the projection 50", and the left-side and right-side corners 147", 148" of the engagement recess 14" are not cut off as in the first embodiment, but are simply rounded.

Figure 15C:
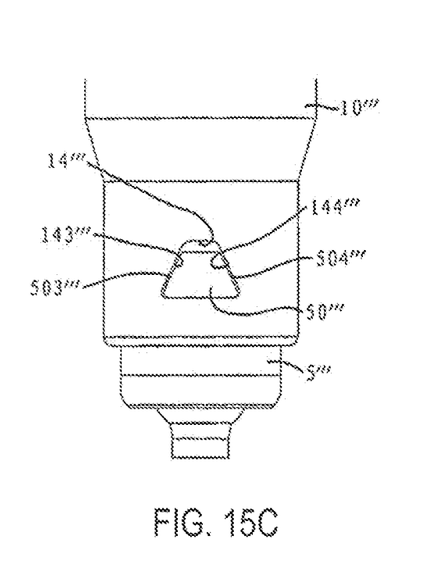
FIG. 15C shows a further modified embodiment of an instrument attached to a receiving part in a side view.

With reference to FIG. 15C, the left-side and right-side corners of each of the projection 50''' and the engagement recess 14''' are neither cut-off nor substantially rounded, whereas the inclination of the sidewalls 503''' and 504''' conforms with that of the sidewalls 143''', 144''' of the engagement recess 14'''. Herein, a top corner of the projection 50''' is flattened.

Figure 15D:
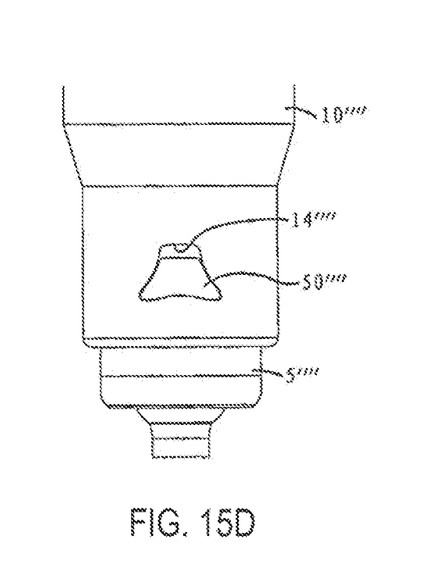
FIG. 15D shows another further modified embodiment of an instrument attached to a receiving part in a side view.
Figure 15E:
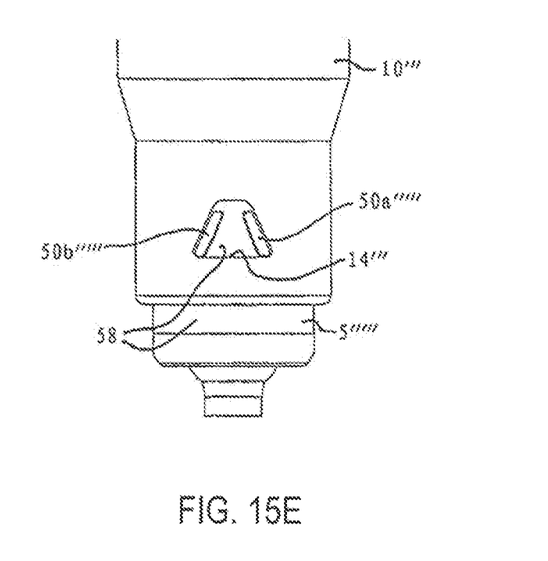
FIG. 15E shows yet another further modified embodiment of an instrument attached to a receiving part in a side view.

With reference to FIG. 15D, the left-side and right-side corners are rounded, respectively, whereas each of the sidewalls of the triangular-shaped projection 50'''' and of the engagement recess 14'''' are convexly or concavely curved, and are configured to mate with each other to provide a form-fit connection. With reference to FIG. 15E, a structure similar to that shown in FIG. 15C is shown, but wherein the projection instead comprises two halves 50a''''', 50b''''' being spaced apart, where each half has a bar-like structure that still maintains the tapered shape of the combined projection as well as the form-fit connection after snap-in.

Those skilled in the art will readily recognize that various further modifications in addition to the above-mentioned modifications are possible and encompassed by the appended claims.

For example, while in the above embodiments, an arrangement with one projection at each respective leg of a receiving part is shown, it is also possible to provide just one projection at one leg of the receiving part (or beneath), while on the other side (or leg) another engagement mechanism such as a projection at the instrument and a recess at the receiving part may be provided, etc.

Further, in the above embodiments, triangular shapes are described with respect to the projections and engagement recesses, respectively, when seen in a plan view. However, other shapes may be encompassed as well, such as oval, semi-circle, trapezoidal, square/rectangular, diamond, or rhombus shapes, etc., may be possible as well. Also, other polygonal shapes are encompassed.

Further, the upper surface 501 of the projection has been described as being flat or following the cylindrical outer contour of the receiving part. However, a convex, planar, concave, dome, or cylindrically shaped upper surface may be possible as well, or analogously to FIG. 15E, a recess can be provided between the outer side walls of the projection.

Moreover, in the above embodiments, receiving parts having a generally cylindrical outer contour have been described. However, the generally cylindrical contour may only apply to partial sections of the receiving part, while other portions of the receiving part may be provided with considerably different outer contours.

In the above embodiments, receiving parts of polyaxial or monoaxial bone anchoring devices have been described. However, other receiving parts which are not configured for connection with an anchoring element for insertion in a bone may also be encompassed by the invention.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part of a bone anchoring device, the receiving part having a first end, a second end opposite to the first end, and a central axis extending through the first end and the second end, and comprising:
    a channel adjacent to the first end for receiving a bone fixation element, wherein the channel forms two free legs each having an engagement structure for engaging a locking element to lock the bone fixation element in the channel;
    an outer surface portion that faces away from the central axis; and
    at least one projection configured to engage an engagement recess of an instrument to provide a connection between the instrument and the receiving part, wherein the at least one projection projects radially outwardly from the outer surface portion, is spaced apart axially from the first end of the receiving part, is spaced apart circumferentially from the channel on one side by a first region of the outer surface portion, and is spaced apart circumferentially from the channel on an opposite side by a second region of the outer surface portion, and has an outwardly facing surface with at least a portion having a same contour as the first and second regions of the outer surface portion when viewed in a cross-section perpendicular to the central axis;
    wherein the at least one projection comprises a first side wall that faces and is inclined relative to the first end as the first side wall extends circumferentially around the central axis to form a region of the at least one projection that widens as the at least one projection extends axially away from the first end, and a lower side wall that faces the second end of the receiving part, wherein an entire circumferential width of the lower side wall extends circumferentially around the receiving part at a constant axial height of the receiving part.

2. The receiving part according to claim 1, wherein the at least one projection and the engagement recess of the instrument are configured to engage in a form-fit engagement.

3. The receiving part according to claim 1, wherein the at least one projection has a triangular shape when viewed in a direction perpendicular to the central axis.

4. The receiving part according to claim 1, wherein at least part of the outer surface portion of the receiving part around the at least one projection and at least part of the outwardly facing surface of the at least one projection have cylindrical contours.

5. The receiving part according to claim 1, wherein the at least one projection further comprises a second side wall that is inclined towards the first end as the second side wall extends circumferentially around the central axis, and wherein the first and second side walls are configured to guide and align the instrument when the instrument is attached to the receiving part.

6. The receiving part according to claim 5, wherein the first and second side walls are symmetric with respect to each other about an axis parallel to the central axis.

7. The receiving part according to claim 5, wherein the first and second side walls converge at a tip portion of the at least one projection that faces the first end of the receiving part.

8. The receiving part according to claim 1, wherein the lower side wall is provided with an undercut.

9. The receiving part according to claim 1, wherein the at least one projection comprises two projections, with one of the projections being provided on each of the legs.

10. A receiving part of a bone anchoring device, the receiving part having a first end, a second end opposite to the first end, and a central axis extending through the first end and the second end, and comprising:
    a channel adjacent to the first end for receiving a bone fixation element, wherein the channel forms two free legs each having an engagement structure for engaging a locking element to lock the bone fixation element in the channel;
    an outer surface portion that faces away from the central axis; and
    at least one projection configured to engage an engagement recess of an instrument to provide a connection between the instrument and the receiving part, wherein the at least one projection projects radially outwardly from the outer surface portion, is spaced apart axially from the first end of the receiving part, and has a circumferential width that is less than a circumferential width of each of the legs;
    wherein the at least one projection comprises an outwardly facing surface with an outer perimeter, where less than half of the entire outer perimeter is chamfered, a first side wall that faces and is inclined relative to the first end as the first side wall extends circumferentially around the central axis to form a region of the at least one projection that widens as the at least one projection extends axially away from the first end, and a lower side wall that faces the second end of the receiving part, wherein an entire circumferential width of the lower side wall extends circumferentially around the receiving part at a constant axial height of the receiving part.

11. A system comprising the receiving part according to claim 10 and the instrument, the instrument comprising a holding member configured to hold the receiving part, wherein the holding member comprises a first arm and a second arm that are movable relative to each other between an open position in which the receiving part is insertable between the first arm and the second arm, and a closed position in which the receiving part is configured to be held between the first arm and the second arm, and wherein at least one of the first arm or the second arm comprises the engagement recess configured to engage the at least one projection of the receiving part.

12. The system according to claim 11, wherein the holding member is tubular.

13. The system according to claim 11, wherein a guiding channel comprising opposing side walls is formed at an inner wall portion of each of the first and second arms, and wherein the guiding channel extends between a free end of a respective one of the arms and the engagement recess of the respective arm, and is configured to guide the at least one projection to the engagement recess.

14. The system according to claim 13, wherein when the at least one projection is positioned in the guiding channel, the arms are expanded into the open position, and wherein when the at least one projection is received in the engagement recess, the arms assume the closed position.

15. The system according to claim 13, wherein a bottom surface of the guiding channel is inclined with respect to a central axis of holding member, such that the inclined bottom surface is engageable with the chamfer on the at least one projection to guide the at least one projection to the engagement recess.

16. The system according to claim 11, wherein the inner wall portion of the arms is provided with a cylindrical contour which mates with a cylindrical contour of the receiving part.

17. A method of connecting a receiving part of a bone anchoring device to an instrument, the receiving part having a first end, a second end opposite to the first end, and a central axis extending through the first end and the second end, and comprising a channel adjacent to the first end for receiving a bone fixation element, wherein the channel forms two free legs each having an engagement structure for engaging a locking element to lock the bone fixation element in the channel, an outer surface portion that faces away from the central axis, and at least one projection that projects radially outwardly from the outer surface portion, that is spaced apart axially from the first end of the receiving part, is spaced apart circumferentially from the channel on one side by a first region of the outer surface portion, and is spaced apart circumferentially from the channel on an opposite side by a second region of the outer surface portion, and that has an outwardly facing surface with at least a portion having a same contour as the first and second regions of the outer surface portion when viewed in a cross-section perpendicular to the central axis, wherein the at least one projection comprises a first side wall that faces and is inclined relative to the first end as the first side wall extends circumferentially around the central axis to form a region of the at least one projection that widens as the at least one projection extends axially away from the first end, and a lower side wall that faces the second end of the receiving part, wherein an entire circumferential width of the lower side wall extends circumferentially around the receiving part at a constant axial height of the receiving part, the instrument comprising a holding member comprising a first arm, a second arm, and an engagement recess at at least one of the first or second arms, the method comprising:

advancing the first arm and the second arm over the first end of the receiving part to insert the receiving part therebetween while the first arm and the second arm are in an open position;

further advancing the receiving part into the holding member until the at least one projection of the receiving part engages the engagement recess of the instrument, while the first arm and the second arm assume a closed position to hold the receiving part therebetween, thereby connecting the instrument to the receiving part.

* * * * *